US010620198B2

(12) United States Patent
Woodhead et al.

(10) Patent No.: US 10,620,198 B2
(45) Date of Patent: Apr. 14, 2020

(54) DEVICE PLATFORM FOR POINT OF CARE TESTING

(71) Applicant: Invitron Limited, Monmouth, Monmouthshire (GB)

(72) Inventors: Andrew James Woodhead, Monmouth (GB); James Stuart Woodhead, Raglan (GB)

(73) Assignee: Invitron Limited, Monmouth, Monmouthsh (GB)

( * ) Notice: Subject to any disclaimer, the term of this patent is extended or adjusted under 35 U.S.C. 154(b) by 0 days.

(21) Appl. No.: 16/328,475

(22) PCT Filed: Aug. 29, 2017

(86) PCT No.: PCT/GB2017/052522
§ 371 (c)(1),
(2) Date: Feb. 26, 2019

(87) PCT Pub. No.: WO2018/046890
PCT Pub. Date: Mar. 15, 2018

(65) Prior Publication Data
US 2019/0346438 A1    Nov. 14, 2019

(30) Foreign Application Priority Data

Sep. 9, 2016 (GB) .................................. 1615320.7

(51) Int. Cl.
*G01N 33/543* (2006.01)
*B01L 3/00* (2006.01)

(52) U.S. Cl.
CPC .... *G01N 33/54366* (2013.01); *B01L 3/50273* (2013.01); *B01L 2200/16* (2013.01);
(Continued)

(58) Field of Classification Search
CPC .......... G01N 33/54366; B01L 3/50273; B01L 2200/16; B01L 2300/069; B01L 2300/0816; B01L 2400/0406; B01L 2400/0481
(Continued)

(56) References Cited

U.S. PATENT DOCUMENTS 5,223,219 A    6/1993  Subramanian et al.
5,726,013 A    3/1998  Clark
(Continued)

FOREIGN PATENT DOCUMENTS

WO    WO 01/84153 A2     11/2001
WO    WO 2007/106579 A2   9/2007

OTHER PUBLICATIONS

Search Report issued in Great Britain Application No. 1615320.7, dated Jun. 30, 2017 (4 Pages).
PCT/GB2017/052522 International Search Report and Written Opinion dated Jan. 5, 2018 (25 pages).

*Primary Examiner* — Benjamin R Whatley
*Assistant Examiner* — Jacqueline Brazin
(74) *Attorney, Agent, or Firm* — Klarquist Sparkman, LLP (57) ABSTRACT

The invention concerns a cartridge for performing sample analysis in a portable point of care test device (POCT); a point of care assay device, comprising said cartridge and a reader for accommodating said cartridge, for detecting and/or quantifying an analyte in a sample; and a kit of parts comprising the said components of said point of care assay device.

31 Claims, 5 Drawing Sheets

(52) U.S. Cl.
 CPC . *B01L 2300/069* (2013.01); *B01L 2300/0816* (2013.01); *B01L 2400/0406* (2013.01); *B01L 2400/0481* (2013.01)

(58) Field of Classification Search
 USPC ......................................................... 422/414
 See application file for complete search history.

(56) References Cited

U.S. PATENT DOCUMENTS

| | | |
|---|---|---|
| 2003/0040021 A1 | 2/2003 | Clark et al. |
| 2007/0087357 A1 | 4/2007 | Clark et al. |
| 2008/0038810 A1* | 2/2008 | Pollack ............. B01L 3/502784 435/283.1 |
| 2009/0148933 A1* | 6/2009 | Battrell ............... B01F 11/0071 435/287.2 |
| 2010/0261286 A1* | 10/2010 | Kim .................. B01L 3/502707 436/149 |
| 2011/0053289 A1* | 3/2011 | Lowe .................... B01L 3/5027 436/501 |
| 2012/0258472 A1* | 10/2012 | Roy ........................ G01N 33/49 435/7.9 |
| 2012/0261286 A1* | 10/2012 | Holloway .......... B65D 85/1054 206/268 |
| 2014/0273187 A1* | 9/2014 | Johnson ................. C12Q 1/001 435/287.2 |
| 2015/0285794 A1* | 10/2015 | Maerkl ................. B01L 3/5027 506/9 |
| 2017/0113221 A1* | 4/2017 | Hoffman .......... G01N 35/00069 |

* cited by examiner

Step 1: Add label reagent

Step 2: Incubate (10 min)

Step 3: Remove sample and label reagent

Step 4: Add wash solution

DEVICE PLATFORM FOR POINT OF CARE TESTING

CROSS REFERENCE TO RELATED APPLICATIONS

This is the U.S. National Stage of International Application No. PCT/GB2017/052522, filed Aug. 29, 2017, which was published in English under PCT Article 21 (2), which in turn claims the benefit of Great Britain Application No. 1615320.7, filed Sep. 9, 2016.

FIELD OF THE INVENTION

The invention concerns a cartridge for performing sample analysis in a portable point of care test device (POCT); a point of care assay device, comprising said cartridge and a reader for accommodating said cartridge, for detecting and/or quantifying an analyte in a sample; and a kit of parts comprising the said components of said point of care assay device.

BACKGROUND OF THE INVENTION

Laboratory tests on biological samples have traditionally been used for diagnosis, screening, disease staging, forensic analysis, pregnancy testing, drug testing, and other reasons. While a few qualitative tests, such as pregnancy tests, have been reduced to simple kits for the patient's home use, a large number of quantitative tests still require elaborate procedures that often necessitate the expertise of trained technicians in a laboratory setting using sophisticated instruments. In recent years, some of these tests have been made available for point of care (POC) analysis by using handheld testing devices that embody sensors and computational electronics for sample analysis.

Point of care tests (POCT) are therefore 'near patient' diagnostic tests performed outside the routine analytical laboratory. A POCT carried out near the patient is advantageous as it can potentially provide rapid results which enable medical practitioners to act sooner, save lives, improve patient outcomes and reduce overall costs to the healthcare system.

An example of a typical POC device is based on a lateral flow immunoassay that relies on the use of a capture reagent immobilised on a membrane (such as a nitrocellulose strip) to capture an analyte from a sample, which analyte transits the membrane by a process of lateral flow/capillary action. The capture reagent is typically an antibody and the bound analyte is normally detected by means of a second antibody labelled with a visually detectable substance such as colloidal gold. This approach has been widely used in POCTs, for example self-tests for pregnancy involving the detection of human chorionic gonadotrophin (HCG) in urine. Generally speaking, immunoassay POCTs have been used in applications where high sensitivity is not required, so that labels providing visual end points have been highly successful. Results can be reported visually (e.g. HCG pregnancy test) or using an electronic reader (e.g. Alere DDS2 drugs of abuse test system).

It is now widely appreciated that the reduced turnaround time associated with a POCT is a highly desirable goal where extremely high sensitivity of detection is needed to detect trace quantities of certain analytes or compounds. However, conventional lateral flow methods using colloidal gold as an end point cannot provide the required sensitivity. Unfortunately, the high sensitivity of detection provided by routine laboratory analysers often involves complex instrumentation which is not appropriate for near patient testing. This has led to significant and increasing interest in microfluidic (lab on a chip) methods. To date, a very small proportion of microfluidic based POCT concepts have come to market: most notably, the Abbott i-STAT Cardiac Troponin (an enzyme immunoassay carried out on a few drops of blood for early detection of angina and coronary artery occlusion) and the Alere Triage CTnI (fluorescence immunoassay) tests.

Therefore, it is widely acknowledged that current POCTs lack the analytical performance of standard laboratory tests and this leads to a compromise in the value they provide, or has led to complex and expensive systems to achieve such sensitivity. A key example is the measurement of cardiac troponin as a marker for myocardial infarction, where analytical sensitivity can be a factor limiting rapid and accurate diagnosis, thus necessitating the use of a clinical chemistry laboratory. There is therefore a need for a technology that can deliver rapid, high sensitivity POCT in the rapidly growing area of clinical diagnostics.

Chemiluminescence based on acridinium esters (AE) offers one of the most sensitive endpoints developed for immunoassays and genetic probe assays and has been applied in the routine clinical laboratory for a wide range of analytes. The high sensitivity of assays based on AE labels derives from the fact that the chemiluminescence output can be detected against a background that is virtually zero. To take advantage of this sensitivity in practice, there is a requirement that all unreacted label must be removed from the site of reaction prior to initiating the chemiluminescent reaction i.e. the use of AE technology requires a clean separation of signal/background. Thus, conventional assay methods utilising AE labelling techniques typically involve several washing steps to remove unbound AE label (background) and so achieve the desired signal specificity. In this regard typical POCT assay formats do not permit adequate washing of specifically bound labelled antibody to ensure that this requirement for AE detection is met. As a consequence, to date, there have been no successful applications of this sensitive technology in a point-of-care format.

Using novel technology we herein provide a POCT based on a clear separation between signal/background that thus provides the requisite sensitivity for use in a high sensitivity assay.

STATEMENTS OF INVENTION

According to a first aspect of the invention there is provided a cartridge for performing sample analysis comprising: a plurality of compartments wherein
  a first compartment comprises at least one reaction chamber for holding the sample and having attached to at least a part of its surface a capture reagent;
  a second compartment comprises at least one receptacle for housing a at least one reagent wherein said reagent is in fluid communication with said first reaction chamber; and
  a third compartment, integral with said first or second compartment or separate therefrom, comprising an extraction device in fluid and/or operable communication with said reaction chamber for removing reagent and/or unreacted products from said reaction chamber.

In a preferred embodiment said extraction device comprises wicking or absorbent material, a capillary tube/feed or a negative pressure device. Most preferably the cartridge comprises wicking or absorbent material mounted on a member and movable with respect to said member so that said wicking/material can be advanced and/or retracted into said reaction chamber.

Preferably, said sample is a biological sample. Reference herein to a biological sample refers to any sample isolated from the body of a subject including, but not limited to, a cell, a population of cells, a biopsy, a tissue, an organ, blood, plasma, serum, sputum, peritoneal fluid, CSF, synovial fluid, sperm, breast milk, bronchial lavage fluid, amniotic fluid, malignant ascites, pleural fluid, seminal fluid, tears, urine, faeces and saliva.

Alternatively, said biological sample may be a cell line or the supernatant fluid from cells maintained in culture medium.

Reference herein to a capture reagent refers to any substance or reagent that can bind, reversibly or irreversibly, to the target analyte in said biological sample (by capturing it from the biological sample). In this manner, as will be appreciated by those skilled in the art, a biological sample having, or suspected of having, the target analyte is added by a user to at least one reaction chamber wherein said analyte (if present) is specifically recognized and bound by the capture reagent, such that it can be used to identify and/or quantitate the analyte In a preferred embodiment of the first aspect of the invention, said capture reagent includes, but is not limited to, antibodies, aptamers and fragments thereof, oligonucleotides or other specific ligands or receptors comprising a specific binding partner for the target analyte in the biological sample.

In a further preferred embodiment of the invention, said capture reagent is bound directly onto at least a part of a surface of the reaction chamber by any means known to those skilled in the art, such as but not limited to, immobilisation by adsorption or by chemical coupling.

Alternatively, said capture reagent is bound indirectly onto at least a part of a surface of the reaction chamber by the use of an anchor substance that binds the capture reagent. Therefore, in this embodiment at least a part of the surface of said reaction chamber is coated with the anchor substance and said capture reagent comprises a binding partner that binds the anchor substance. Most ideally, said anchor substance is selected from the group comprising: avidins, oligo and polynucleotides, proteins or lectins which bind a binding partner on the capture reagent and therefore cause the capture reagent to bind to at least a part of a surface of the reaction chamber.

As is known to those skilled in the art, avidins are a member of a family of proteins, including avidin, streptavidin, and neutravidin, functionally defined by their ability to bind biotin with high affinity and specificity, which serves as their specific binding partner. The binding affinity of avidins to biotin, albeit noncovalent, is so high that it can be considered irreversible. Therefore, in this embodiment, said capture reagent is biotinylated. Many agents can be biotinylated typically by chemical or enzymatic means and are well known to those skilled in the art. Most ideally, said biotinylated capture reagent is a biotinylated antibody.

Lectins are naturally occurring carbohydrate specific binding proteins which selectively bind carbohydrate groups such as typical sugar moieties. Lectins perform recognition at the cellular and molecular level and play numerous roles in biological recognition phenomena involving cells, carbohydrates, and proteins. Therefore, in this embodiment, said lectins bind to carbohydrate groups of the capture reagent such as, but not limited to, those occurring on antibodies and fragments thereof.

Oligo and polynucleotides can bind to capture reagents through complementary nucleotide molecules and these complementary nucleotides can be used to modify capture reagents in order to elicit the requisite binding.

More ideally, said anchor substance is an avidin and said capture reagent comprises a biotin binding partner or vice versa. Most ideally, said anchor substance is streptavidin and said capture reagent comprises a biotin binding partner or vice versa.

In yet a further preferred embodiment of the first aspect of the invention, said reaction chamber is in the form of a well comprising a base wherein said base is coated with the capture reagent and/or anchor substance.

In yet a further preferred embodiment still, said first compartment comprises a plurality of reaction chambers.

In a further preferred embodiment, said first compartment comprises a reaction chamber in the form of a well to the bottom of which are attached a plurality of capture reagents, ideally at discreet sites, each specific for a different target analyte in said sample. As will be appreciated by those skilled in the art, this will permit the analysis of a number of different analytes in a single sample. Moreover, it will be appreciated by those skilled in the art that light output from spatially separated sources can be resolved by the use of various light measurement technologies such as, but not limited to, CCDs, CMOS sensors and photodiode arrays In another preferred embodiment, the contents of the reaction chamber are mixed during incubation. Agitation methods may involve shaking or vibration of the cartridge, magnetic mixing of particles or stirring element, or other agitation methods such as, but not limited to, sonication.

It will be appreciated by one skilled in the art that the capture reagent or anchor substance may be coupled to paramagnetic particles which may be added to the reaction chamber as a suspension. A preferred embodiment of the invention involves the introduction of target analyte and a particulate capture reagent wherein the particles may be removed from suspension by suitably arranged electromagnets prior to the removal of unreacted components.

In a further preferred embodiment, said second compartment comprises a plurality of receptacles for housing a number of different reagents wherein each receptacle is in fluid communication with the reaction chamber. Alternatively, said cartridge comprises a number of further compartments wherein at least one includes at least one receptacle for housing a reagent wherein said reagent is in fluid communication with said reaction chamber. Ideally, all of said further compartments includes at least one receptacle.

In a preferred embodiment, said reagent includes, but is not limited to, a washing reagent, labelling or labelled reagent, detection reagent, capture reagent, or the like.

Reference herein to washing reagent refers to solutions containing buffering agents, surfactants and other compounds designed to reduce non-specific binding of the labelled reagent.

Reference herein to a labelling or labelled reagent refers to any reagent that binds the target analyte, wherein said labelling or labelled reagent is directly, or indirectly, linked to an indicator or labelling system such as an enzyme that catalyses colour development, a chromophore or a luminophore (e.g. a fluorescent, phosphorescent, bioluminescent or chemiluminescent marker); a modulator of emissions from a fluorescent, phosphorescent, chemiluminescent or bioluminescent molecule or ion; a co-factor for a chemiluminescent or bioluminescent reaction; a detectable micro or nanoparticle such as, but without limitation, a coloured or magnetic particle. More preferably, indicator or labelling systems include, but are not limited to, conventional ELISA systems or bioluminescent, chemiluminescent or pigmented indicator systems. Most preferably, said labelling or labelled reagent includes, but is not limited to, antibodies, aptamers and fragments thereof, or other specific ligands or receptors and said labelling reagent comprises an acridinium ester forming part of a chemiluminescent labelling system.

Reference herein to detection reagent refers to any agent that is required to initiate a luminescent reaction, such as a bioluminescent or chemiluminescent reaction. Said reagent can be an oxidizing agent, a catalyst or a substrate, for example, acridinium esters undergo a light-emitting reaction in the presence of an oxidizing agent in alkaline conditions, thus a detection reagent includes an oxidizing agent and/or an alkaline solution. As will be appreciated by those skilled in the art, the nature of the detection reagent will be dependent upon the nature of the indicator or labelling system. Most preferably, said detection agent is for detection of a chemiluminescent label which undergoes a light emitting reaction following the sequential addition of hydrogen peroxide in acid and an alkaline solution, thus the said detection reagent is hydrogen peroxide in acid and/or an alkaline solution.

Further, as will be appreciated by those skilled in the art, in embodiments wherein said capture reagent is coated indirectly onto at least a part of a surface of the reaction chamber by use of an anchor substance that binds the capture reagent, said capture reagent can be housed in the receptacle. In this manner, said capture reagent can then be added to the reaction chamber wherein it then binds to the anchor substance. Advantageously, when using a plurality of reaction chambers, this permits different capture agents to be added to different reaction chambers for the detection of different analytes. Further, this is advantageous from a manufacturing viewpoint, as a single anchor substance can be used to coat each reaction chamber which can then be provided with a different capture reagent according to the different analytes to be detected.

In a preferred embodiment at least one of said receptacles houses washing reagent, at least one of said receptacles houses detection reagent, and at least one of said receptacles houses capture reagent. More ideally, at least one of said receptacles houses washing reagent, at least one of said receptacles houses a first detection reagent, at least one of said receptacles houses a second detection reagent, at least one of said receptacles houses a capture reagent, and at least one of said receptacles houses labelling reagent. Most ideally, the first detection reagent is hydrogen peroxide in acid, the second detection reagent is an alkali solution, the capture reagent is a biotinylated antibody, and the labelling reagent is an AE labelled antibody.

In yet a further preferred embodiment said receptacle includes a pump for pumping said reagent into said reaction chamber. Optionally, said receptacle also includes a valve for controlling the flow of reagent into said reaction chamber. The cartridge may include a single pump that controls movement of different fluids (e.g. the different reagents and/or a fluid sample), or alternatively, a plurality of pumps, one of which, for example, controls movement of the fluid sample, and at least one of which controls movement of the plurality of different reagents. In one aspect, the cartridge includes a plurality of pumps, and movement of each of the different fluids is controlled by a different pump.

In an alternative embodiment, each reagent is housed in a sealed pouch contained within the receptacle, said pouch being in close proximity to a conduit leading to the reaction chamber. The application of pressure to the pouch by an activator causes it to release its contents into the conduit and deliver them to the said reaction chamber.

The order and timing of flow of any one or more reagent(s) to the reaction chamber may vary depending on the test being employed as well as the type of fluid contained in the respective receptacle(s).

In one embodiment, the first receptacle comprises a labelling or labelled reagent, a second receptacle comprises a wash reagent, and a third receptacle comprises a detector reagent. In such an embodiment, a sample to be analysed is added to the reaction chamber and any target analyte in the sample is reacted, either sequentially or simultaneously, with a labelled reagent and said capture reagent. As will be apparent to those skilled in the art, only a portion of the added labelled reagent may be captured in this way. To ensure any unreacted materials are removed, fluid in the reaction chamber is removed using the absorbent material which is advanced into the reaction chamber. Consequently, only labelled reagent that is attached to captured analyte is bound to the reaction chamber and will remain. Optionally, a wash reagent can be deployed, either before or after the use of the aforementioned absorbent material. Used in this way, a wash reagent helps to remove unbound analyte and unwanted materials, so reducing residual background noise. Thus, the absorbent material is used to remove the liquid in the reaction chamber. This wash step can be repeated as necessary. Lastly, detection reagent is added, the nature of which will depend upon the type of labelling or labelled reagent utilized. Measurement of the emitted light signal can then be used to detect and quantify target analyte in the sample.

As will be appreciated, in alternative embodiments wherein an anchor substance is used to bind capture reagent to the reaction chamber, the cartridge may further comprise an additional receptacle comprising the capture reagent which can be added to the reaction chamber prior to first use of the absorbent material in order that the capture reagent can bind to the anchor substance. Preferably, the capture reagent is added at the same time as the labelling or labelled reagent.

In a preferred embodiment said absorbent material is mounted on a spool whose circular motion, in a first direction, advances said material and whose circular motion, in an opposite direction, retracts said material. Alternatively said material is mounted on a conveyor whose motion, in a first direction, advances said material and whose motion, in an opposite direction, retracts said material. Ideally, said movable member is arranged such that said material, when advancing, dips into the reaction chamber and, when retracting, is removed from said reaction chamber.

In certain embodiments of the invention said movable member is associated with a blade that cuts said absorbent material after it has been used.

In alternative embodiments of the invention to ensure any unreacted materials are removed from the reaction chamber, fluid in the reaction chamber is removed using a suction device or via a capillary flow device.

In yet a further preferred embodiment, said cartridge further comprises a control device that synchronises the flow of reagents to the reaction chamber and the use of said absorbent material or suction device or capillary flow device. Ideally, the control device ensures reagents flow into the reaction chamber and, optionally, remain there for a selected incubation time, after which said absorbent material or suction device or capillary flow device is used to extract any fluid remaining in the chamber and not bound to the capture reagent provided on, or coated on, the reaction chamber surface.

Typically, the biological sample will contain a target analyte of interest. The determination, detection and/or quantitation of said analyte in the biological sample is performed within the cartridge. This analysis could be, for example, determination of analytes specific for different disorders such as, but not limited to, chronic metabolic disorders, such as blood insulin, proinsulin or C-peptide (diabetes); markers of other specific diseases including acute diseases, such as cardiac disease markers (e.g. cardiac troponin-, NT-ProBNP), markers of thyroid function (e.g., determination of thyroid stimulating hormone (TSH)), tumour markers and markers of infectious agents and the like.

Typically, an analytical procedure will be carried out in which the target analyte in a sample is reacted with one or more binding partners that provide a means of capture as well as one or more binding partners that are labelled with a detectable substance such that, following said reaction, the amount of said detectable substance is a function, or inverse function, of the amount of said analyte present in said sample. In a preferred aspect of the invention, the binding partners will be antibodies and the detectable substance will be a compound capable of taking part in a luminescent reaction such as a bioluminescent or chemiluminescent reaction.

In a more preferred aspect to the invention, the detectable substance will be an acridinium ester which will be detected or quantified following the addition of hydrogen peroxide in acid and an alkaline solution.

In a further aspect to the invention, more than one analyte will be detected in the same reaction chamber by the use of antibodies specific for the detection of each analyte wherein said antibodies are labelled with acridinium esters which are chemically modified so as to provide individual light emission characteristics with regard, for example, to wavelength or reaction kinetics such that each labelled antibody can be quantified independently of each other labelled antibody in the same reaction chamber.

In a further preferred embodiment of the invention the cartridge comprises an agitation member for mixing the contents of the reaction chamber. As will be appreciated by those skilled in the art, agitation of the reaction vessel will ensure a maximum rate of reaction of the component reagents. Such agitation may be achieved for example by linking the reaction chamber to a vibration motor, incorporating a magnetic stirrer within the reaction chamber or physically moving the reaction chamber by other means.

According to a second aspect of the invention, there is provided a point of care assay device comprising the cartridge as herein disclosed and a reader adapted to enable the cartridge to be placed in functional communication with said reader. For example, the cartridge may be inserted into, placed on or attached to the reader and the reader may comprise docking means, such as a slot, or alignment means to enable the cartridge to be inserted, placed or attached appropriately to the reader.

In a preferred embodiment of the second aspect of the invention, said reader comprises a detector for detecting the capture reagent and/or labelling or labelled reagent. As will be appreciated by those skilled in the art, the nature of the detector will vary depending upon the nature of indicator or labelling system of the capture agent and/or the nature of the labelling reagent. For example, changes in fluorescence intensity or wavelength can be monitored using a fluorimeter and analogous changes in chemiluminescence monitored using a luminometer. Most ideally, said detector is an optical detector for measuring light emission. Additionally, or alternatively, said cartridge comprises a detector.

In a further preferred embodiment of the second aspect of the invention, said reader comprises a motor that is configured to engage the moveable member of said cartridge when the cartridge is inserted into the reader and thereby provide for advancement and retraction of said absorbent material.

In a further preferred embodiment of the second aspect of the invention, said reader comprises a motor that is configured to operate the suction device and thereby provide for removal of fluid from said reaction chamber.

Optionally, said reader may comprise a control device that synchronises the flow of reagents to the reaction chamber and the use of said motor. Ideally, the control device controls the flow of reagents into the reaction chamber and, optionally, their resident time there for a selected incubation time, after which said control device controls the movement of said absorbent material or the suction of said suction device to extract any fluid remaining in the chamber and not bound to the capture reagent.

In a further preferred embodiment of the second aspect of the invention there is provided an agitation member for mixing the contents of the reaction chamber. Such agitation may be achieved for example by linking the reaction chamber to a vibration motor, incorporating a magnetic stirrer within the reaction chamber or physically moving the reaction chamber by other means. This function is ideally also controlled by the reader. Additionally, the reader is configured so that such agitation can be applied to subsequent washing steps to ensure maximum removal of unreacted component reagents.

According to a third aspect of the invention, there is provided a kit of parts for a point of care assay device comprising:
 at least one cartridge as herein disclosed; and
 at least one reader adapted to functionally communicate with said cartridge whereby assay reagents in said cartridge can be used to provide a POCT for identifying at least one analyte in a biological sample.

Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

The Invention will now be described by way of example only with reference to the Examples below and to the following Figures wherein:

FIGS. 3A-3E show a cartridge of the invention being used in an immunoassay. Specifically.

FIGS. 4A-4E show a cartridge of the invention being used in a chemiluminescent immunoassay after addition of a sample to the reaction chamber (FIG. 3). Specifically.

DETAILED DESCRIPTION

Figure 1A:
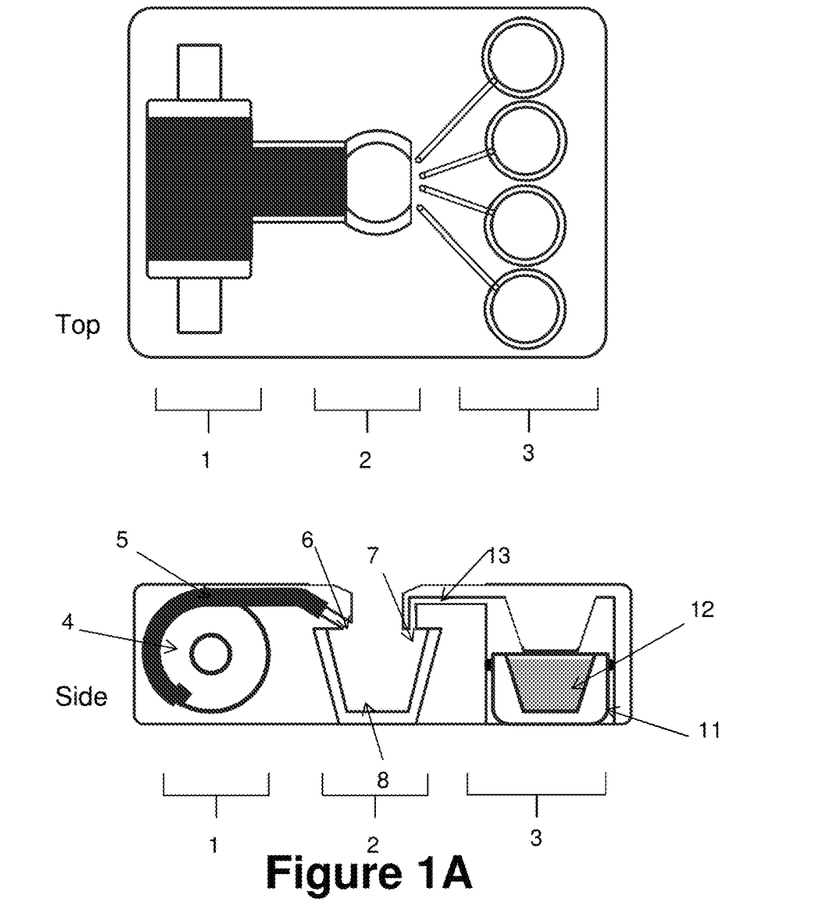
FIG. 1A shows a diagrammatic illustration of a top and side elevation view of cartridge for use according to the invention.

Referring now to the figures and, firstly, to FIG. 1, part A, there is shown a side view of a cartridge comprising compartments 1, 2, and 3. Compartments 1 and 3 are positioned either side of 2 and connect to it via openings 6 and 7. In the embodiment shown each compartment has a different function. 1 houses a spool 4 on which is wound a length of absorbent material 5. Rotation of spool 4 in a first (clockwise) direction advances material 5 towards compartment 2 and, via opening 6, material 5 is able to enter 2. In contrast, rotation of spool 4 in a second (anticlockwise) direction retracts material 5 away from compartment 2. Notably, although reagent removal is illustrated by means of wicking material wound on spool 4 other mechanisms, known to those skilled in the art, may be used to remove reagents from compartment 2 such as, without limitation, the use of wicking, capillary forces or negative pressure or the like.

Compartment 2 comprises a reaction chamber 8 in the form of a well, or the like. Chamber 8 has attached to its inner lower surface 9 a capture reagent (not shown). This reagent is bound to chamber 8 directly, using chemical or other attractive forces, alternatively (and more typically) this reagent is bound indirectly to chamber 8 using an intermediate in the form of an anchor substance which, in turn, is bound to chamber 8 directly, using chemical or other attractive forces. In use, the cartridge is supplied with the capture reagent already attached to chamber 8 or in a receptacle for subsequent use.

Compartment 3 comprises a receptacle 11 housing a reagent 12. Receptacle 11 is in fluid communication with chamber 8 via conduit 13 and opening 7. The nature of the reagent housed in receptacle 11 is determined having regard to the nature of the analyte to be assayed and/or the nature of the detection system to be used. Although not shown, receptacle 11 also comprises a pump device whereby the reagent contained therein can be selectively moved to chamber 8.

The invention thus far described represents the simplest version of the cartridge. In other embodiments said cartridge is provided with further receptacles 11a, 11b, 11c etc. for housing a plurality of different reagents all for use in the assay of the invention. Additionally, or alternatively, said cartridge is provided with further reaction chambers 8a, 8b, 8c etc. for undertaking a number of assays simultaneously or successively. Whatever the complexity of the cartridge, it is configured so that at least one supply of absorbent material or one suction device or one capillary flow member makes removable contact with one reaction chamber 8, and at least one receptacle 11 housing at least one reagent is in fluid communication with said reaction chamber 8.

Figure 1B:
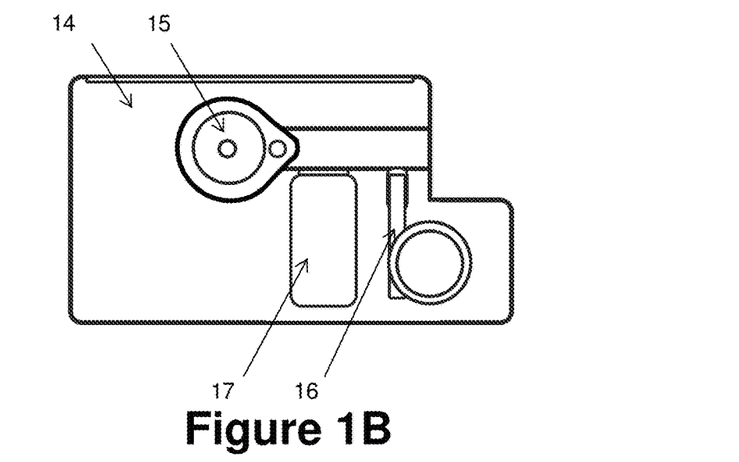
FIG. 1B shows a diagrammatic illustration of a side elevation view of reader for use according to the invention.

Part B of FIG. 1 shows a reader 14 adapted to accommodate the aforementioned cartridge. In this particular illustration, reader 14 is provided with a cavity suitably sized and shaped to accommodate the cartridge, moreover, reader 14 is also provided with co-operating devices that interact with the cartridge to ensure reagents and material 5 are moved to chamber 8 in a synchronised and timely manner. Specifically, in certain embodiments, said reader 14 may be provided with a motor 15 to rotate spool 4, although alternative arrangements can equally be utilised. Further, the reader can optionally comprise an actuator 16 for initiating flow of reagent 12 from receptacle 11. Further, a detector 17, such as an optical detector, may be included for detecting readouts from the reaction chamber 8 for analyte detection and/or quantitation. Alternative detectors 17 may be used and the choice will be determined by the nature of the label and capture agents utilised.

Figure 2:
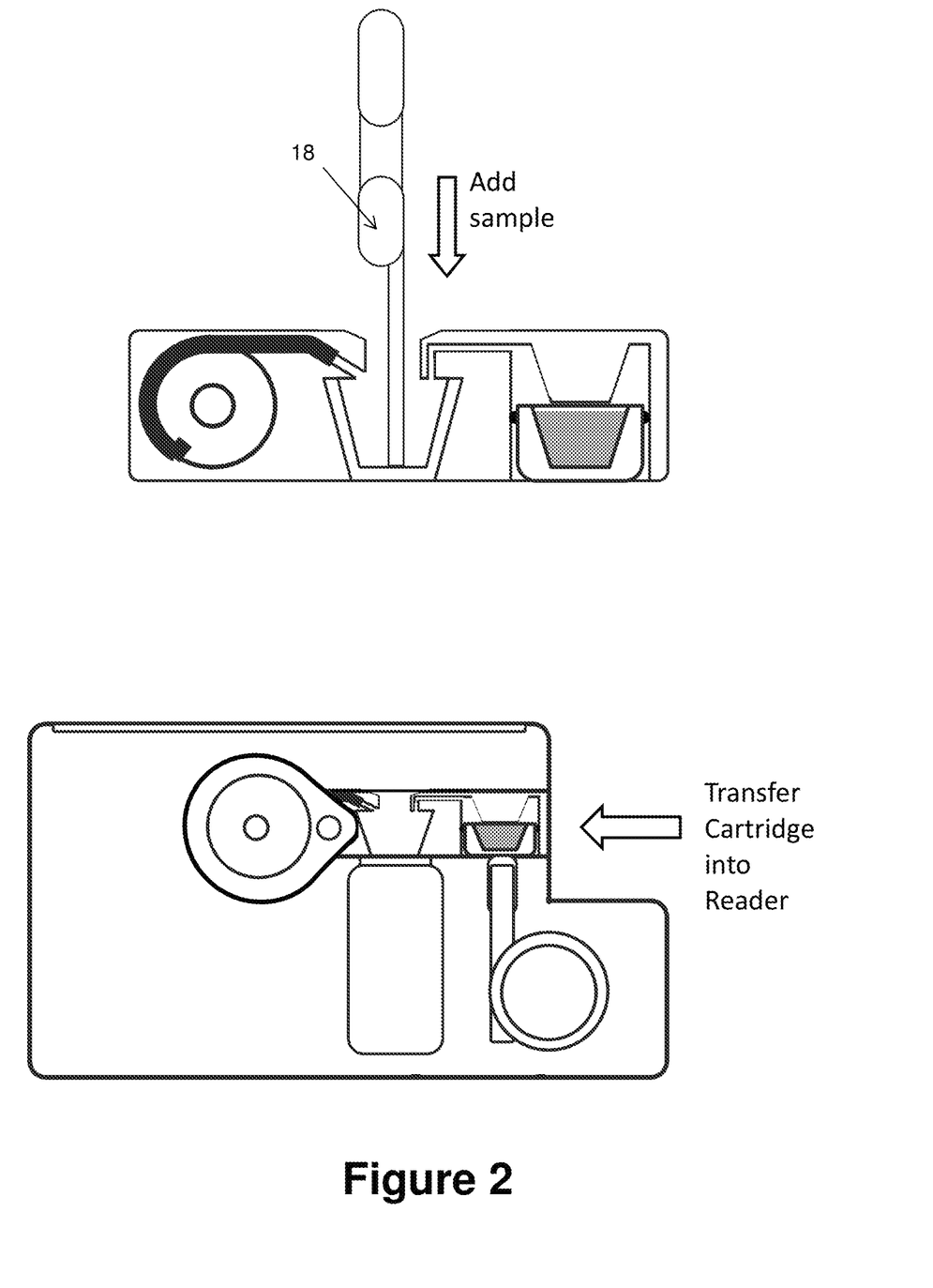
FIG. 2. Shows a diagrammatic illustration of a side elevation view of cartridge for use according to the invention demonstrating the steps illustrating how the invention is worked.
Figure 3A:
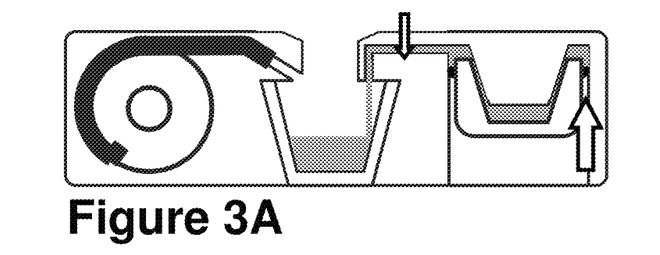
FIG. 3A shows antibody that recognises analyte being added to the reaction chamber.
Figure 3B:
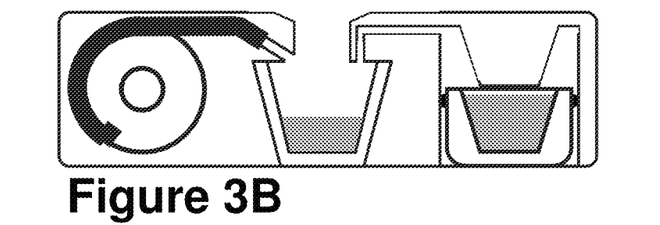
FIG. 3B shows an incubation interval.
Figure 3C:
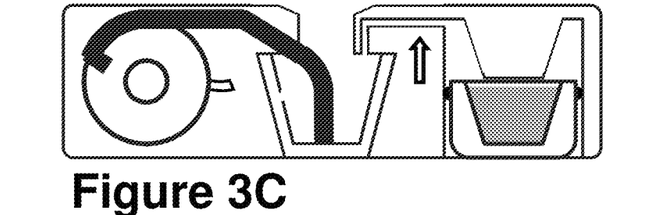
FIG. 3C shows removal of reaction fluid using absorbent material.
Figure 3D:
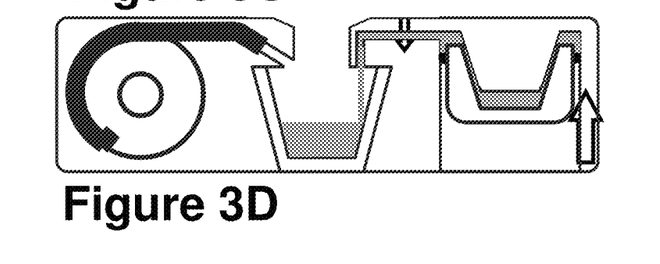
FIG. 3D shows a wash step.
Figure 3E:
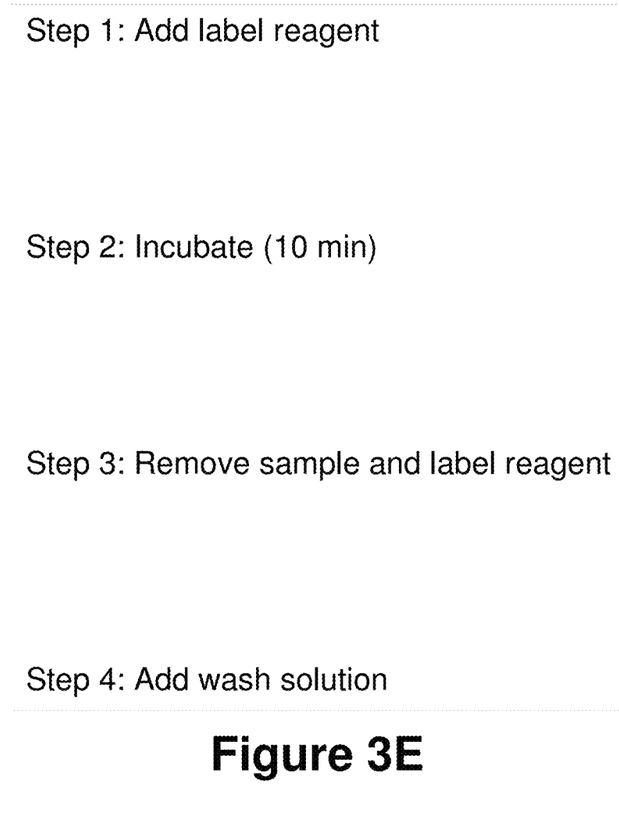
FIG. 3E shows steps illustrating how the invention is worked.
Figure 4A:
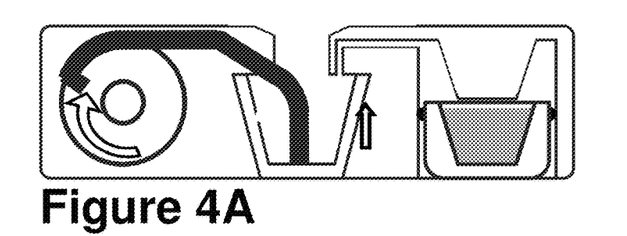
FIG. 4A shows a repeat wash.
Figure 4B:
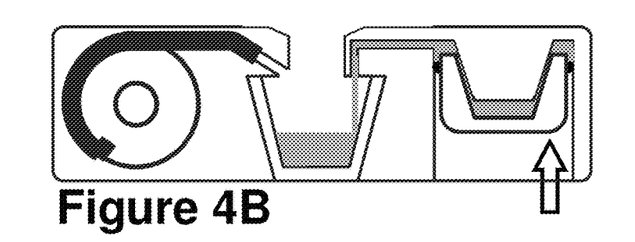
FIG. 4B shows addition of a detection reagent to the reaction chamber.
Figure 4C:
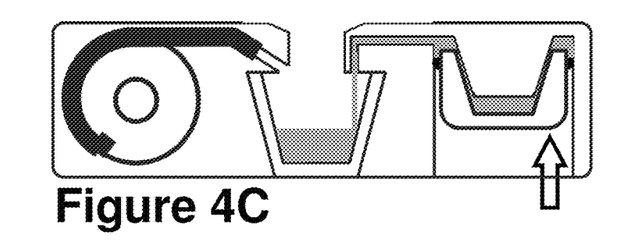
FIG. 4C shows addition of a second detection reagent to the reaction chamber.
Figure 4D:
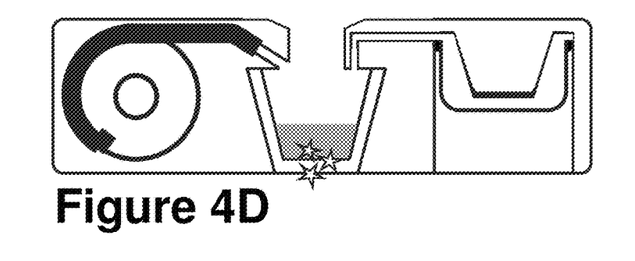
FIG. 4D shows the emittance of a reaction signal.
Figure 4E:
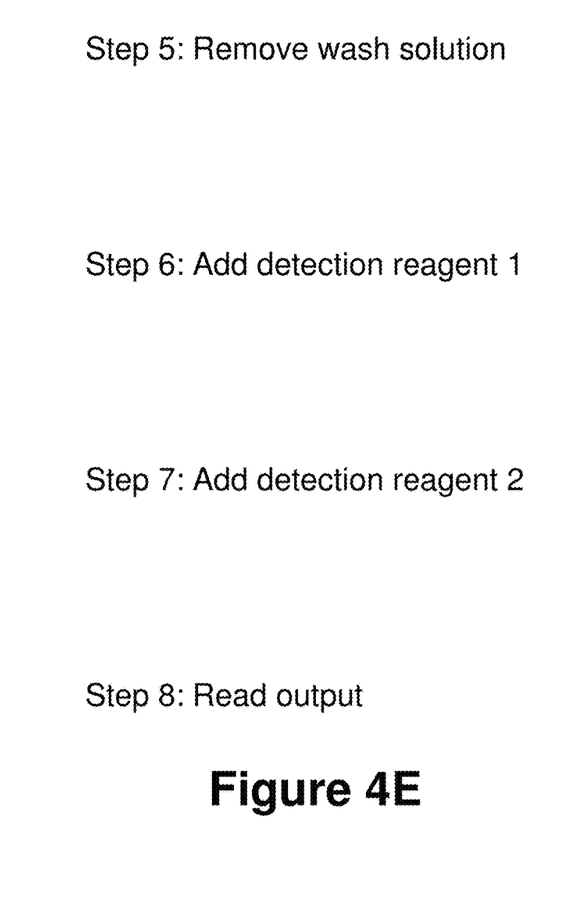
FIG. 4E shows steps illustrating how the invention is worked.

As shown in FIG. 2, in use, biological sample 18 is added to chamber 8 which is then positioned within reader 14. Reader 14 is then activated and it controls the addition of reagents to chamber 8 and, ultimately, takes a reading of any analyte detected in sample 18.

FIG. 3 illustrates use of the cartridge in an immunoassay. Chamber 8 is provided with a capture reagent. After a sample has been added to chamber 8, detector AE labelled antibody that recognises the analyte is added to chamber 8 (FIG. 3A) and incubated for a predetermined amount of time (FIG. 3B), after which, material 5 is dipped in chamber 8 to remove reaction fluid (FIG. 3C). This last step may be performed by a suction device or a capillary device. Optionally, fluid removal this is followed by at least one washing step (FIG. 3D) and a further dipping/removal step as wash solution is supplied to chamber 8 from a further receptacle 11 and material 5 is re-dipped in chamber 8 (repeat FIG. 3C) or a suction device is activated. These steps are shown by FIG. 3e.

FIG. 4 shows that the wash step is repeated (FIG. 4A), in this embodiment, 3 times (the existence of and number of wash steps will be determined having regard to the nature of the assay and the relative affinity of the reagents for the analyte). After the washing is complete i.e. when one can be sure unused reactants have been removed, at least one detection reagent is added to chamber 8, in this example a first (FIG. 4B) and then a second detection reagent (FIG. 4C) is added to chamber 8. These reagents trigger the emittance of a signal (FIG. 4D) that is read by reader 14 and is indicative of the amount of analyte captured by said capture reagent and so present in said biological sample.

If preferred, said reader can be calibrated prior to its use using known amounts of the analyte to be detected.

An illustrated embodiment of the invention will now be described in general terms to illustrate the working of the invention.

Typically, the cartridge is supplied with a layer of anchor substance coated on the bottom of chamber 8. Advantageously, this substance is of a general type such as an avidin, lectin or an oligonucleotide. Further receptacles 11a, 11b, 11c etc. are charged or contain suitable regents having regard to the nature of the analyte to be detected and/or the nature of the assay reaction. However, at least one of the receptacles contains capture reagent that binds both the anchor substance and the analyte to be detected. At least one other receptacle contains detection reagent that also binds the analyte but itself emits a signal when activated or works in conjunction with at least one other reagent in one other receptacle to emit a signal when activated. Moreover, material 5 is typically supplied in a retracted form. Ideally also, one receptacle comprises a wash solution.

In use, biological sample 18 is added to chamber 8 and the cartridge is inserted in reader 14. Reader 14 then controls the order and timing of the addition of one or more reagents from one or more receptacles 11 to chamber 8. When a desired reaction is over, wash solution, if desired, is added to chamber 8 and reader 14 then controls the dipping of material 5 in chamber 8 to withdraw unused/excess reaction fluid. Those skilled in the art will appreciate that binding of capture reagent (directly or indirectly) to chamber 8 results in analyte being retained in chamber 8 after use of material 5. Accordingly, at least one detector reagent can then be added to chamber 8 and conditions supplied (via the use of other reagents or a suitable trigger) to initiate the emittance of a signal indicative of the nature and/or amount of analyte captured on the capture reagent.

Illustrated embodiments of the invention will now be described in more specific terms to illustrate the working of the invention.

Example 1 Detection of Cardiac Troponin as a Marker for Myocardial Infarction Materials and Methods Measurement of Troponin I Using the Test Cartridge Monoclonal antibodies to cardiac troponin I (cTnI) were obtained from Hytest (Turku, Finland). Antibodies were labelled with 2,6-dimethyl-4-(N-succinimidyloxycarbonyl) phenyl 10-methyl-acridinium-9-carboxylate trifluoromethanesulfonate. (AE). Typically, antibodies were reacted in aqueous solution with AE for 15 minutes and the product purified by gel filtration. AE labelled antibodies were stored in a buffer containing bovine serum albumin and sodium azide.

Biotinylated antibodies were prepared by reacting antibodies in aqueous solution with biotin-LC-LC-N-hydroxysuccinimide (Life Technologies, Renfrew, UK) for 18 h and the product purified by gel filtration. Biotinylated antibodies were stored in buffer containing bovine serum albumin and sodium azide.

Polystyrene reaction chambers were coated with streptavidin (Sigma-Aldrich, Poole, UK) at a concentration of 5 µg/ml in a dilute carbonate/bicarbonate buffer. Wells were coated overnight at a temperature of 4° C. Reaction chambers were washed (3×300 µl) with phosphate buffered saline (PBS) containing the detergent tween-20 (0.1%) and then blocked with PBS containing bovine serum albumin (1%) for a period of 2 h at room temperature. After decanting the fluid, plates were dried overnight under reduced pressure. Streptavidin coated plates were stored sealed in foil pouches at a temperature of 2-8° C.

A series of standard concentrations of cTnI were prepared by addition of recombinant cardiac troponin (Abcam, Cambridge, UK) to horse serum (Sigma Aldrich, Poole, UK). 1 ml aliquots were lyophilised in glass vials which were stoppered under vacuum. Lyophilised standards were stored at 2-8° C.

For assay purposes, individual streptavidin coated reaction chambers were assembled into fabricated test cartridges. Sample (50 µl) and a mixture of AE-labelled and biotinylated antibodies (50 µl) were introduced into the reaction chamber and the reaction allowed to proceed for 10 minutes. The reaction mixture was then removed from the well by brief lowering of the wick. Wash buffer (100 µl) was added from the appropriate port and then removed by wicking. This wash was repeated twice more and the luminescent reaction was initiated by injection of hydrogen peroxide (0.5%) in nitric acid (0.1M) followed by injection of 0.25M sodium hydroxide. Total light emission integrated over a 1 second time period was measured using a photomultiplier tube. Results are shown in Table 1. As shown serial dilutions of cTnI in human plasma yielded a response parallel to the troponin standards over the concentration range 6-390 µg/ml. These results indicate that this rapid assay could be applied to the measurement of low levels of cTnI in human samples with minimal or no background interference.

TABLE 1

Rapid assay using the disclosed device for the measurement of cTnI in human plasma based on the use of a chemiluminescent labelled antibody and a biotinylated antibody that was captured onto streptavidin coated reaction wells. Serial dilutions of cTnI in human plasma yielded a response parallel to the troponin standards over the concentration range 6-390 pg/ml. These results were comparable to procedures when using conventional reagent washing and indicate that this rapid assay could be applied to the measurement of low levels of cTnI in human samples.

| Relative Concentration in Plasma (%) | Mean RLU | Measured cTnI (pg/ml) |
|---|---|---|
| 100 | 4985 | 390.1 |
| 50 | 2830 | 187.8 |
| 25 | 1780 | 86.1 |
| 12.5 | 1240 | 42.6 |
| 6.25 | 930 | 21.6 |
| 3.12 | 810 | 13.5 |
| 1.56 | 700 | 6.1 |

Example 2 Measurement of Intact Proinsulin Using the Test Cartridge

Figure 5:
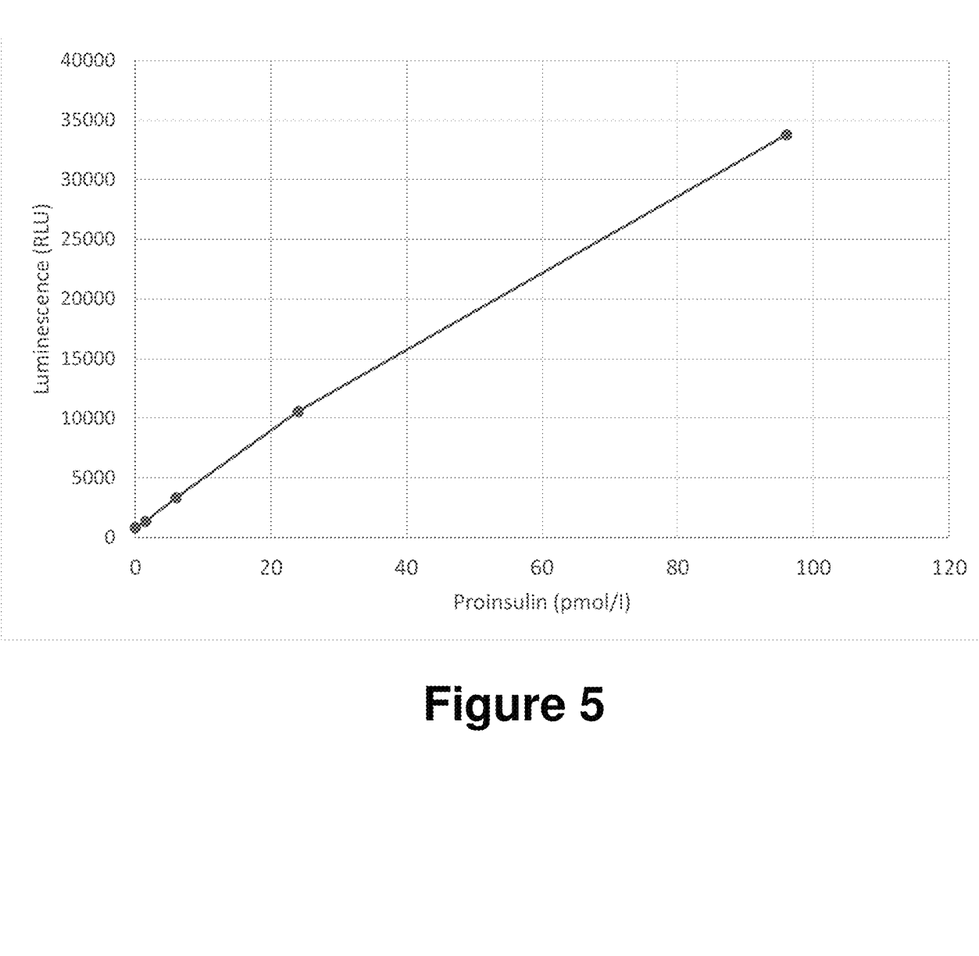
FIG. 5 shows the read out of the device of the invention when used to measure proinsulin.

A series of standard concentrations of human proinsulin (1$^{st}$ International Reference Preparation 84/611, NIBSC, Potters Bar, EN6 3QG, UK) were prepared in horse serum. For assay purposes, individual streptavidin coated reaction chambers were assembled into fabricated test cartridges, Samples (25 µl) and a mixture of AE-labelled and biotinylated antibodies (100 µl) were introduced into the reaction chamber and the reaction allowed to proceed for 10 minutes. The reaction mixture was then removed and washing carried out as described in the previous example. The luminescent reaction was initiated as described above and measurement carried out for a period of 1 second. Results are shown in FIG. 5 and results on 7 test samples are shown in Table 2. Results are compared with those obtained in a conventional (3 h) intact proinsulin microplate immunoassay (ELISA).

TABLE 2

Results of Test Samples when measuring Intact Proinsulin using the Test Cartridge.

| Sample No | POCT | ELISA |
|---|---|---|
| 1 | 2.3 | 2.0 |
| 2 | 16.2 | 16.2 |
| 3 | 3.9 | 3.8 |
| 4 | 16.8 | 16.8 |
| 5 | 8.4 | 9.6 |
| 6 | 1.5 | 1.6 |
| 7 | 12.8 | 16.4 |

Example 3 Comparison of Wells Washed in the Cartridges of the Invention with Wells Washed with a Laboratory Plate Washer Cartridges were assembled with streptavidin coated wells and a mixture of AE-labelled and biotinylated proinsulin antibodies (100 µl) added to each. The labelled antibody added to each well gave a luminescence reading of 3,416,600 RLU in a laboratory microplate luminometer. After 15 minutes, the wells were washed by means of the cartridge wick mechanism (3×150 µl wash buffer). Wells were then removed and light output measured in a laboratory luminometer. Results were compared with wells to which had been added the same antibody mixture, but which were then washed in a laboratory plate washer. As shown in Table 3, the residual activity was essentially the same (namely 0.02% of the added luminescence activity).

TABLE 3

Comparison of cartridge washing with conventional well washing (residual luminescence-RLU).

| Cartridge Wash | Laboratory Washer (Duplicates) | |
|---|---|---|
| 790 | 730 | 770 |
| 720 | 710 | 690 |
| 680 | 690 | 720 |
| 750 | 730 | 580 |
| 930 | 680 | 700 |
| 730 | 620 | 700 |
| 840 | 710 | 750 |
| 870 | 690 | 660 |
| Mean = 789 | Mean = 696 | |

The invention claimed is:

1. A cartridge for performing sample analysis, comprising a plurality of compartments, wherein
   a first compartment comprising at least one reaction chamber for holding a sample and having attached to at least a part of its surface a capture reagent;
   a second compartment comprising at least one receptacle for housing at least one reagent, wherein said at least one reagent is in fluid communication with said first compartment; and
   a third compartment, integral with said first or second compartment or separate therefrom, comprising an extraction device in fluid and/or operable communication with said at least one reaction chamber for removing said at least one reagent and/or unreacted products from said at least one reaction chamber, wherein said extraction device comprises wicking or absorbent material mounted on a conveyor which is movable in a first direction, to advance said wicking or absorbent material and, in an opposite direction to retract said wicking or absorbent material into or from said at least one reaction chamber.

2. The cartridge according to claim 1, wherein said wicking or absorbent material is mounted on said conveyor in the form of a spool whose circular motion, in a first direction, advances said wicking or absorbent material and whose circular motion, in an opposite direction, retracts said wicking or absorbent material.

3. The cartridge according to claim 1, wherein said conveyor is arranged such that said wicking or absorbent material, when advancing, dips into the at least one reaction chamber and, when retracting, is removed from said at least one reaction chamber.

4. The cartridge according to claim 1, wherein said conveyor is associated with a blade that cuts said wicking or absorbent material.

5. The cartridge according to claim 1, wherein said sample is a biological sample.

6. The cartridge according to claim 1, wherein said capture reagent is a substance or reagent that can bind, reversibly or irreversibly, to a target analyte in said sample.

7. The cartridge according to claim 6, wherein said capture reagent is selected from the group consisting of: antibodies, aptamers and fragments thereof, oligonucleotides, and other specific ligands or receptors for the target analyte.

8. The cartridge according to claim 1, wherein said capture reagent is bound directly onto at least a part of a surface of the at least one reaction chamber.

9. The cartridge according to claim 1, wherein said capture reagent is bound indirectly onto at least a part of a surface of the at least one reaction chamber by the use of an anchor substance that binds the capture reagent.

10. The cartridge according to claim 9, wherein said anchor substance is selected from the group consisting of: avidins, oligonucleotides, polynucleotides, proteins and lectins.

11. The cartridge according to claim 10, wherein said anchor substance is avidin and said capture reagent comprises a biotin binding partner, or vice versa.

12. The cartridge according to claim 10, wherein said anchor substance is streptavidin and said capture reagent comprises a biotin binding partner, or vice versa.

13. The cartridge according to claim 1, wherein said at least one reaction chamber is in the form of a well comprising a base wherein said base is coated with the capture reagent and/or an anchor substance.

14. The cartridge according to claim 1, wherein the at least one reaction chamber of said first compartment comprises
   a plurality of reaction chambers, or
   one reaction chamber in the form of a well to the base of which are attached a plurality of capture reagents each specific for a different target analyte in said sample.

15. The cartridge according to claim 1, wherein the capture reagent and/or an anchor substance are coupled to paramagnetic particles.

16. The cartridge according to claim 1, wherein said second compartment comprises a plurality of receptacles for housing a number of different reagents wherein each receptacle is in fluid communication with the at least one reaction chamber.

17. The cartridge according to claim 1, wherein said cartridge comprises a number of further compartments wherein at least one of said number of further compartments includes at least one receptacle for housing a further reagent wherein said reagent is in fluid communication with said at least one reaction chamber.

18. The cartridge according to claim 1, wherein said at least one reagent of the second compartment is a washing reagent, labelling or labelled reagent, detection reagent, the capture reagent, or a second capture reagent.

19. The cartridge according to claim 18 wherein said at least one reagent is a labelling or labelled reagent, and said labelling or labelled reagent is an enzyme; a chromophore; a luminophore; a modulator of emissions from a fluorescent, phosphorescent, chemiluminescent or bioluminescent molecule or ion; a co-factor for a chemiluminescent or bioluminescent reaction; a coloured particle; a magnetic particle; ELISA system; pigmented indicator system; antibodies; aptamers and fragments thereof; or an acridinium ester (AE) molecule.

20. The cartridge according to claim 18, wherein said at least one reagent is a detection reagent and said detection reagent is hydrogen peroxide in acid or an alkaline solution.

21. The cartridge according to claim 16, wherein
at least one of said plurality of receptacles houses a washing reagent, at least one of said plurality of receptacles houses a detection reagent, and at least one of said plurality of receptacles houses a labelling or labelled reagent or capture reagent, or
at least one of said plurality of receptacles houses a washing reagent, at least one of said receptacles houses a first detection reagent, at least one of said receptacles houses a second detection reagent, at least one of said receptacles houses the capture reagent or a second capture reagent, and at least one of said receptacles houses labelling or labelled reagent.

22. The cartridge according to claim 21, wherein the first detection reagent is hydrogen peroxide in acid, the second detection reagent is an alkali solution, the capture reagent is a biotinylated antibody, and the labelling reagent is an AE labelled antibody.

23. The cartridge according to claim 1, wherein
said at least one receptacle includes at least one pump for pumping said reagent into said at least one reaction chamber, and/or
said at least one receptacle includes a valve for controlling the flow of reagent into said at least one reaction chamber.

24. The cartridge according to claim 1, wherein each of said at least one reagent is housed in a sealed pouch contained within the at least one receptacle, said pouch being in close proximity to a conduit leading to the at least one reaction chamber whereby application of pressure to the pouch by an activator causes said pouch to release its contents into the conduit and deliver their contents to the said at least one reaction chamber.

25. The cartridge according to claim 1, wherein said cartridge further comprises a control device that synchronises the flow of reagents to the at least one reaction chamber and the use of said wicking or absorbent material.

26. The cartridge according to claim 1, wherein said cartridge further comprises an agitation member whereby components in said at least one reaction chamber are mixed.

27. A point of care assay device comprising the cartridge of claim 1, and a reader adapted to enable the cartridge to be placed in functional communication with said reader.

28. The point of care assay device according to claim 27, wherein
said reader comprises a docking or alignment means to enable the cartridge to be inserted, placed or attached to the reader.

29. The point of care assay device according to claim 27, wherein said reader comprises
a detector for detecting the capture reagent and/or a labelling or labelled reagent;
a motor that is configured to engage the conveyer of said cartridge when the cartridge is inserted into the reader and thereby provide for advancement and retraction of wicking or absorbent material;
a control device that synchronises the flow of said at least one reagent to the at least one reaction chamber and the use of said wicking or absorbent material and/or said motor; and/or
a device that causes agitation of the at least one reaction chamber or its contents following the introduction of the at least one reagent and/or wash solutions.

30. A kit of parts for a point of care assay (POCT) device comprising:
at least one cartridge according to claim 1; and
at least one reader adapted to functionally communicate with said cartridge whereby said at least one reagent and said capture reagent in said cartridge provide a POCT for identifying at least one analyte in a biological sample.

31. A point of care assay device comprising the cartridge of claim 27, wherein the reader comprises a detector for detecting the capture reagent.

* * * * *